United States Patent [19]

Shlichta

[11] Patent Number: 4,922,807
[45] Date of Patent: May 8, 1990

[54] BALLAST SYSTEM FOR MAINTAINING CONSTANT PRESSURE IN A GLOVE BOX

[75] Inventor: Paul J. Shlichta, San Pedro, Calif.

[73] Assignee: The United States of America as represented by the Administrator of the National Aeronautics and Space Administration, Washington, D.C.

[21] Appl. No.: 414,812

[22] Filed: Sep. 29, 1989

[51] Int. Cl.⁵ .............................................. B64D 13/00
[52] U.S. Cl. ...................................... 98/1.5; 98/115.3
[58] Field of Search .................... 55/DIG. 18; 98/1.5, 98/115.3

[56] References Cited

U.S. PATENT DOCUMENTS

| | | |
|---|---|---|
| 1,642,577 | 9/1927 | Carson .............................. 98/1.5 X |
| 2,741,410 | 4/1956 | La Violette . |
| 2,786,740 | 3/1957 | Taylor . |
| 3,907,389 | 9/1975 | Cox . |
| 4,026,286 | 5/1977 | Trexler . |
| 4,111,753 | 9/1978 | Folsom . |
| 4,304,224 | 12/1981 | Fortney . |
| 4,704,951 | 11/1987 | Pruchon .............................. 98/1.5 |

Primary Examiner—Harold Joyce
Attorney, Agent, or Firm—Thomas H. Jones; John R. Manning; Charles E. B. Glenn

[57] ABSTRACT

A ballast system for a glove box including a fixed platform on which is mounted an inflatable bag on top of which resides a cover and a weight. The variable gas volume of the inflatable bag communicates with that of the glove box via a valved tube. The weight and gas volume are selected to maintain a relatively constant pressure in the glove box despite variations in the glove box volume while avoiding the use of complicated valving apparatus.

13 Claims, 2 Drawing Sheets

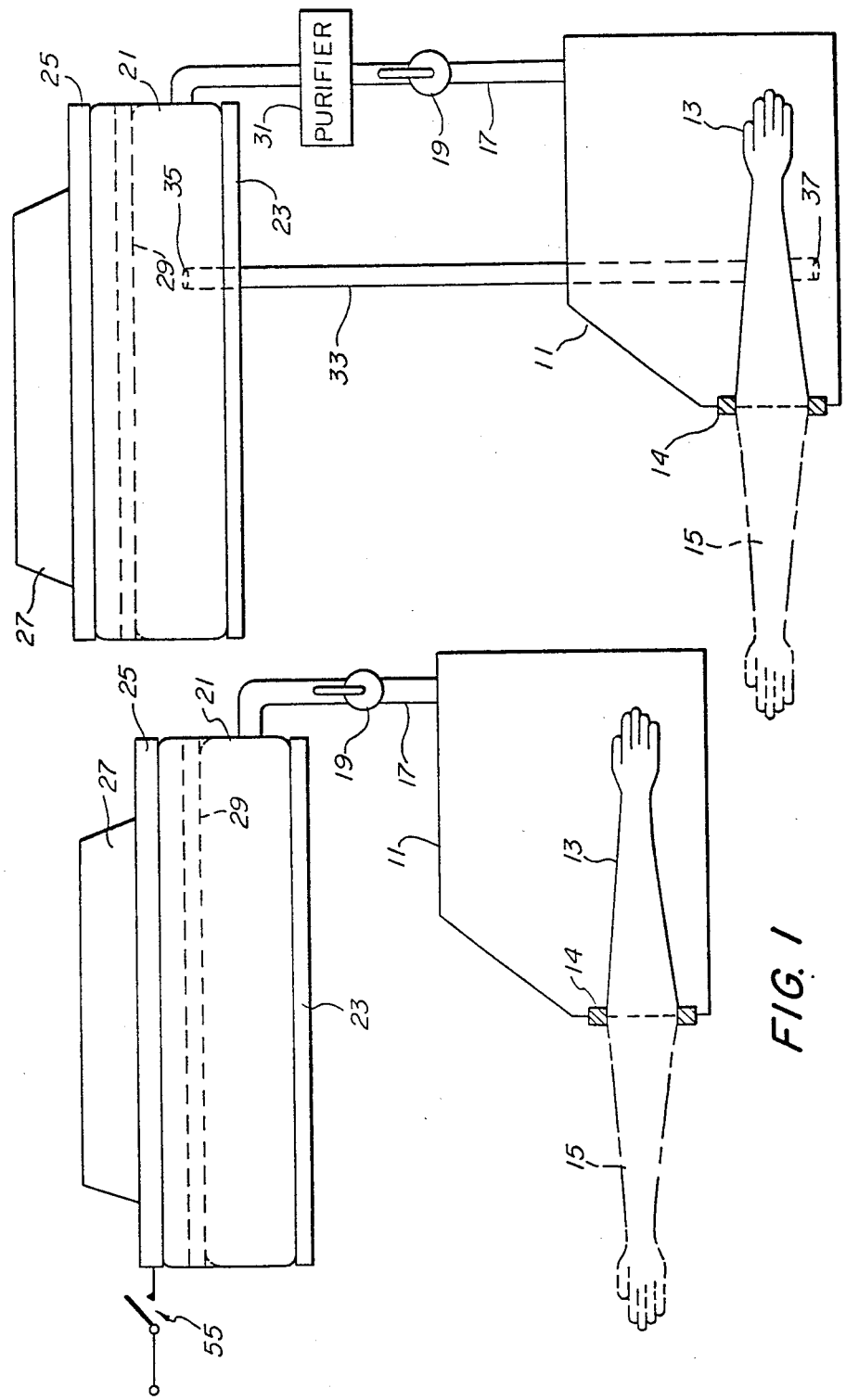

BALLAST SYSTEM FOR MAINTAINING CONSTANT PRESSURE IN A GLOVE BOX

ORIGIN OF THE INVENTION

The invention described herein was made in the performance of work under a NASA contract, and is subject to the provisions of Public Law 96-517 (35 USC 202) in which the Contractor has elected not to retain title.

TECHNICAL FIELD

The present invention relates to the field of isolation enclosures and, more particularly, to a ballast system for maintaining constant pressure in such isolation enclosures.

BACKGROUND ART

A common isolation enclosure used in the prior art is the glove box. At least three types of systems employing glove boxes are known: filter systems, negative systems, and positive systems. Filter systems are those connected to the ambient air by filters. Negative systems are those employing an isolated atmosphere at negative pressure in order to prevent the escape of dangerous materials. Positive systems are those having an isolated atmosphere at positive pressure to prevent the action of ordinary air on reactive materials inside the glove box.

In certain industries, such as the nuclear industry or the pharmaceutical industry, filter systems are used to isolate manufacturing processes from the ambient air, either to prevent the propagation of contaminant products into the atmosphere, or to prevent the introduction of pollutants contained in the atmosphere into the place where the manufacturing process is being performed. Glove boxes employed in such systems are typically ventilated by ventilation networks which permit the control of the rate of flow and of the pressure prevailing in each of them. In the ventilation network, when air is admitted and exhausted, one or more high-efficiency filtration barriers are installed in order to trap the polluting or radioactive dusts.

In negative pressure glove box systems, the gloves are always positioned inside the box. Such systems tend to be less troublesome than positive systems as far as pressure maintenance is concerned.

In positive glove box systems, the gloves typically protrude out of the glove box when not in use as a result of the positive pressure forcing them out. To use the gloves, the hand is inserted into them and the glove is forced into the glove box, against the positive pressure. Since the volume of the box is considerably decreased by the insertion of the glove, the pressure will go up, which results in the operator struggling to move the glove against the higher pressure. When the glove is pulled out, the sudden pressure drop poses a risk of leaks in the system.

To avoid these problems in positive systems and in some negative systems, the prior art has employed expensive valving systems to respond to the pressure changes to maintain a relatively constant pressure. Aside from their considerable expense, such valves tend to break down easily.

Typically, maximum and minimum pressure valves are employed, one connected to a gas source, the other to a vent to the ambient air. Both valves are connected to a pressure sensor. The sensor, valves, and isolation gas source are each a potential source of failure. In particular, failure of the maximum pressure valve could cause an excessively high pressure, which would rip the gloves off the glove box. Failure of the minimum pressure valve could result in a negative pressure, which would allow contaminating ambient air to leak in.

Thus, valves and attendant apparatus used in the prior art are a source of expense and potential breakdowns. Reducing or eliminating such valves would contribute to cheaper, safer systems. Additionally, it would be desirable to avoid waste and replenishment of the gas source used in connection with prior art systems.

STATEMENT OF THE INVENTION

Accordingly, it is an object of the invention to improve isolation enclosure systems;

It is another object of the invention to provide an improved pressure regulation mechanism for isolation enclosures and, particularly, glove boxes;

It is another object of the invention to reduce the cost of and simplify glove box systems; and It is another object of the invention to eliminate valves and associated apparatus used to regulate pressure in glove box systems.

These and other objects and advantages are achieved according to the invention by providing a gas enclosure of variable volume communicating by a tube or duct with the isolation enclosure. Weighting means is provided in conjunction with the gas enclosure to cause the gas enclosure to contract or expand to an appropriate extent to maintain a relatively constant steady state pressure in the isolation enclosure.

A preferred system according to the invention may include:
(1) a variable volume such as a bellows or rubber bag located between two flat plates,
(2) a passive source of constant positive pressure, such as a dead weight on the upper plate or, in special cases such as operation in micro-gravity, a spring system, and
(3) a tube or duct connecting the variable volume to the isolated atmosphere system.

The foregoing preferred system is given by way of illustration only and should not be construed in any way to limit the scope of the invention, which is defined by the appended claims construed according to applicable law.

BRIEF DESCRIPTION OF THE DRAWINGS

The just-summarized invention will now be described in conjunction with the drawings, of which:

FIG. 1 is a schematic side view diagram illustrating the preferred embodiment;

FIG. 2 is a schematic side view diagram illustrating an embodiment employing purification apparatus.

DETAILED DESCRIPTION OF THE INVENTION

Figure 3:
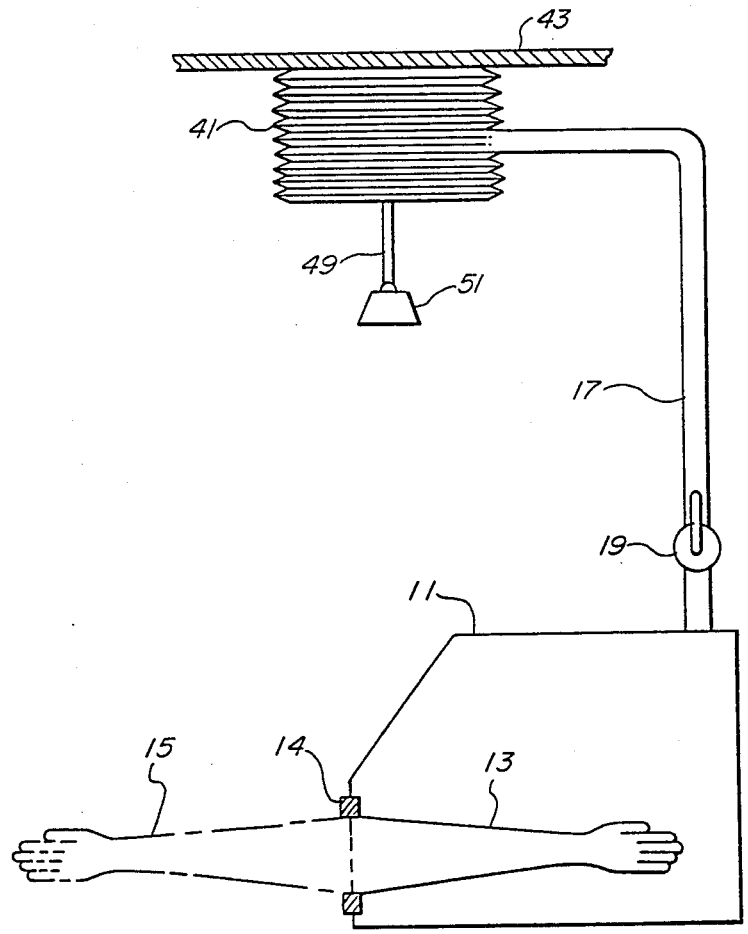
FIG. 3 is a schematic side view diagram illustrating a negative pressure embodiment.

FIG. 1 illustrates an isolation enclosure system employing a conventional glove box 11 including a glove 13 fixed with respect to the glove box 11 by a seal 14. The glove 13 permits sealably introducing a hand or other object into the glove box 11.

According to the preferred embodiment, a tube 17 leads through a valve 19 to an inflatable bag 21 located above the volume of the glove box 11. The inflatable bag 21 rests on a fixed platform 23 disposed above the glove box 11. The platform 23 might also be located below or behind the glove box 11 in various alternative configurations. A cover 25 rests on the top surface of the inflatable bag 21. The cover 25 carries a weight 27.

In the absence of a pressure compensation means, when the glove box 11 is not in use, the glove 13 protrudes out of the glove box 11 at the position indicated by the phantom line 15. When the glove box 11 is in use, the glove 13 lies within the glove box 11 as shown in FIG. 1.

In accordance with the preferred embodiment, pressure compensation is provided by the inflatable bag 21 in conjunction with the fixed platform 23, movable cover 25, and weight 27. This pressure compensation achieves results similar to those of prior art valve systems, but without the expense and complexity.

According to the preferred embodiment of FIG. 1, when the glove 13 is inserted into the glove box 11, and the valve 19 is in the open position, the pressure created is relieved by inflation of the inflatable bag 21 moving the weight 27 upward against the force of gravity. When the glove 13 is removed, the force of gravity deflates the inflatable bag 21, maintaining a relatively constant steady state pressure within the glove box 11.

The inflatable bag 21 is preferably cylindrically shaped, and may be in the shape of a bellows, if desired. It may be fabricated of any conventional plastic material or any material used to form conventional bellows.

In FIG. 1, the glove box 11 may be any conventional or commercially-available glove box unit modified to sealably receive a tube 17. The tube 17 is, in turn, sealably connected to the inflatable bag 21.

The volume of the inflatable bag 21 in the embodiment of FIG. 1 is selected to be a comfortable multiple of the volume of four gloves 13. The multiples may be 2, 3 or 4, resulting in an inflatable bag 21 having a volume of, for example, 16 glove volumes. The glove volume may be simply determined by filling the glove 13 with water, weighing the filled glove 13, and dividing by the weight per unit volume of water. It may be noted that twice the glove volume is the maximum sudden change in pressure for which the unit may be called upon to compensate.

The value of the weight 27 is selected to maintain a constant steady state pressure in the glove box 11. Such a pressure is typically relatively small, on the order of a few ounces per square inch, for example, 0.1 to 1 psi (pounds per square inch). The value of the weight 27 may be simply calculated in a cylindrical embodiment by the relation that the area of the cross-section of the cylinder divided into the sum of the weight of the cover 25 and the weight of the weight 27, is equal to the pressure per square inch applied upon the inflatable bag 21. Thus, for example, if the pressure is 0.1 psi and the total weight of the cover 25 and the weight 27 equals one pound, the area of the cylindrical cross-section is 10 square inches.

FIG. 2 illustrates an embodiment employing a purifier 31 to remove impurities in the air in the glove box 11. Such a purifier 31 may be, for example, a furnace to remove oxygen or various well-known filtering systems used, for example, in biological applications.

The embodiment of FIG. 2 is structurally and functionally equivalent to that of FIG. 1, with the exception of the insertion of the purifier 31 in the feed tube 17 and the provision of a second tube 33. The second tube 33 sealably communicates from one opening 35 in the inflatable bag 21 to a second opening 37 in the glove box 11. In this manner, an interconnected purification system is created wherein the gas in the glove box 11 may be circulated and purified while still retaining the advantages of pressure compensation.

FIG. 3 shows a negative pressure embodiment. The embodiment includes a bellows 41 suspended from a fixed platform 43. A tube 17 having a valve 19 therein sealably communicates between the bellows 41 and a glove box 11. The glove box 11 is the same as that disclosed in connection with FIGS. 1 and 2, except that it operates at negative pressure. For this reason, the weighting employed is suspended from the bellows, rather than placed on top of it as in FIG. 1 and FIG. 2. Accordingly, in FIG. 3, a cord rope or other fastening device 49 extends from the central portion of the bellows 41 and is attached to a weight 51. Thus, in the embodiment of FIG. 3, the weight 51 expands the bellows to provide the desired pressure compensation.

An advantage attendant to either the positive or negative systems described above is that they may be adapted to provide a warning of a pressure change. For example, a position activated safety switch 55 may be added to the movable cover 23, as shown in FIG. 1. Such a modification provides a simple, foolproof warning system. An additional advantage of a negative bellows system is that a negative bellows provides a good way of detecting slow leaks.

As will be appreciated, the just-disclosed embodiments compensate for pressure variations in both positive and negative type glove boxes. They do so while eliminating the use of valves and attendant apparatus required in the prior art, which led to expense and complication.

Those skilled in the art will appreciate that the foregoing preferred embodiments are subject to numerous adaptations and modifications without departing from the scope and spirit of the invention. Therefore, it should be understood that, within the scope of the appended claims, the invention may be practiced other than as specifically described herein.

I claim:

1. An apparatus comprising:
   an isolation enclosure means having means for sealably introducing an object therein;
   a gas enclosure means for providing a variable volume gas enclosure;
   means for communicating gas between said isolation enclosure means and said gas enclosure means; and
   weighting means for operating in conjunction with said gas enclosure means to maintain a substantially constant steady state pressure in said isolation enclosure means in response to changes in volume of the isolation enclosure means.

2. The apparatus of claim 1 wherein said gas enclosure means comprises an inflatable bag.

3. The apparatus of claim 2 wherein said isolation enclosure means comprises a glove box having a flexible glove means attached thereto for insertion therein.

4. The apparatus of claim 3 wherein said means for communicating comprises a first tube means sealably connected to said inflatable bag and to said glove box.

5. The apparatus of claim 3 further including a fixed platform on which said inflatable bag rests.

6. The apparatus of claim 5 wherein said means for communicating further includes:
 a second tube means sealably communicating between said bag and said glove box; and
 filter means interposed in said first tube means for filtering air flowing between said bag and said glove box.

7. The apparatus of claim 4 wherein said first tube means further includes a valve means for opening and closing said first tube means to permit or prevent gas flow in said first tube means, respectively.

8. The apparatus of claim 5 wherein said weighting means comprises a weight placed on top of said inflatable bag.

9. The apparatus of claim 1 wherein said gas enclosure means comprises a bellows.

10. The apparatus of claim 9 further including a fixed platform, wherein said bellows is attached beneath said fixed platform and wherein said weighting means comprises a weight suspended from said bellows.

11. The apparatus of claim 10 wherein said means for communicating comprises tube means for sealably communicating between said isolation enclosure means and said gas enclosure means.

12. A ballast system for an isolation enclosure comprising:
 means for providing a variable gas volume;
 means connected between said variable gas volume and said isolation enclosure for providing gas flow therebetween; and
 a passive weighting means positioned for applying force to vary said gas volume.

13. The ballast system of claim 12 wherein said isolation enclosure comprises a positive glove box system wherein insertion of a glove reduces the volume of the isolation enclosure, and wherein said means for providing and said passive weighting means cooperate to expand said variable gas volume when said glove is inserted into said glove box.

* * * * *